(12) United States Patent
Capistron et al.

(10) Patent No.: US 9,561,961 B2
(45) Date of Patent: Feb. 7, 2017

(54) INJECTABLE FILLERS FOR AESTHETIC MEDICAL ENHANCEMENT AND FOR THERAPEUTIC APPLICATIONS

(75) Inventors: Stephen M. Capistron, Melrose, MA (US); Edward S. Ahn, Dover, MA (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 13/588,809

(22) Filed: Aug. 17, 2012

(65) Prior Publication Data

US 2013/0060230 A1 Mar. 7, 2013

Related U.S. Application Data

(60) Provisional application No. 61/525,391, filed on Aug. 19, 2011.

(51) Int. Cl.

| C08K 3/32 | (2006.01) |
|---|---|
| C08K 5/06 | (2006.01) |
| B44C 1/22 | (2006.01) |
| A61M 5/00 | (2006.01) |
| C08L 5/02 | (2006.01) |
| C01B 25/32 | (2006.01) |
| A61K 8/24 | (2006.01) |
| A61Q 19/08 | (2006.01) |
| A61K 8/04 | (2006.01) |
| A61K 8/73 | (2006.01) |
| A61K 8/90 | (2006.01) |
| A61K 8/02 | (2006.01) |

(52) U.S. Cl.
CPC ............ *C01B 25/327* (2013.01); *A61K 8/0279* (2013.01); *A61K 8/042* (2013.01); *A61K 8/24* (2013.01); *A61K 8/73* (2013.01); *A61K 8/90* (2013.01); *A61Q 19/08* (2013.01); *C01B 25/32* (2013.01); *A61K 2800/594* (2013.01); *A61K 2800/91* (2013.01); *C01P 2004/61* (2013.01); *C01P 2006/12* (2013.01)

(58) Field of Classification Search
None
See application file for complete search history.

(56) References Cited

U.S. PATENT DOCUMENTS

| 3,893,841 | A | 7/1975 | Nijhawan et al. |
|---|---|---|---|
| 6,013,591 | A | 1/2000 | Ying et al. |
| RE39,196 | E | 7/2006 | Ying et al. |
| RE41,584 | E | 8/2010 | Ying et al. |
| 7,968,110 | B2 | 6/2011 | Hubbard |
| 8,029,755 | B2 | 10/2011 | Ahn |
| 2004/0031420 | A1 | 2/2004 | Lin et al. |
| 2004/0185021 | A1* | 9/2004 | Hubbard ............... 424/70.13 |
| 2005/0031704 | A1* | 2/2005 | Ahn ....................... 424/602 |
| 2006/0257358 | A1 | 11/2006 | Wen et al. |
| 2006/0257488 | A1* | 11/2006 | Hubbard ................ 424/486 |
| 2009/0041812 | A1 | 2/2009 | Bell |
| 2010/0136117 | A1 | 6/2010 | De Groot |

FOREIGN PATENT DOCUMENTS

| EP | 0 838 430 A1 | 4/1998 |
|---|---|---|
| EP | 1 787 626 A1 | 5/2007 |
| WO | WO 2005/032456 A2 | 4/2005 |
| WO | WO 2011/009635 * | 1/2011 |
| WO | WO 2011/009635 A1 | 1/2011 |

OTHER PUBLICATIONS

Li et a., "Injectable drug-delivery systems based on supramolecular hydrogels formed by poly(ethylene oxide)s and α-cyclodextrin", Journal of Biomedical Materials Research Part A, 65A(2), 2003, pp. 196-202.*
Gutowska et al., "Injectable Gels for Tissue Engineering," *The Anatomical Record*, 263(4): 342-349 (Jan. 1, 2001).
Zhou et al., "Nanoscale hydroxyapatite particles for bone tissue engineering," *Acta Biomaterialia*, 7(7): 2769-2781 (Mar. 16, 2011).
European Patent Office, International Search Report in International Patent Application No. PCT/US2012/051441 (Mar. 6, 2013).
International Bureau of WIPO, International Preliminary Report on Patentability in International Patent Application No. PCT/US2012/051441 (Feb. 25, 2014).
European Patent Office, Examination Report in European Patent Application No. 12754150.6 (Mar. 6, 2015).

* cited by examiner

*Primary Examiner* — Melissa Javier
(74) *Attorney, Agent, or Firm* — Green, Griffith & Borg-Breen LLP (57) ABSTRACT

The present invention relates to a biocompatible injectable filler composition comprising calcium phosphate particles having a porosity of about 10% to about 90%, a BET surface area of about 1 m²/g to about 100 m²/g, and a mean particle size of about 1 micron to about 30 microns, a thermoreversible hydrophilic gelling agent, a carrier comprising water and an optional persistence enhancer and/or volumizing agent, and methods of its use to restore tissue volume and/or to smooth out tissue defects as in soft tissue or deep tissue augmentation.

14 Claims, 1 Drawing Sheet

INJECTABLE FILLERS FOR AESTHETIC MEDICAL ENHANCEMENT AND FOR THERAPEUTIC APPLICATIONS

CROSS-REFERENCE TO RELATED APPLICATIONS

This patent application claims the benefit of U.S. Provisional Patent Application No. 61/525,391, filed Aug. 19, 2011, which is incorporated by reference.

BACKGROUND OF THE INVENTION

The invention relates to a biocompatible injectable filler composition, such as a dermal filler (e.g., superficial dermal filler, mid-dermal filler or deep dermal filler) or subdermal filler composition, methods for their preparation, and a method of its use in aesthetic medical applications such as tissue augmentation and restoration.

Aesthetic medicine involves the treatment of patients who desire to modify their appearance or desire to reverse aesthetic problems caused by aging, accidents, or malformation. The majority of aesthetic medical treatments involve minimally invasive procedures, such as dermal and subdermal filler injections. A dermal filler is a product that is injected or placed into the dermis. Subdermal fillers are those that are placed underneath the dermis in the subcutis. Desirably the dermal or subdermal filler when injected in the skin or tissue adds bulk to the area of injection restoring or increasing soft-tissue volume. Restoration of facial volume using fillers can rebalance facial proportions, increase symmetry, and reduce wrinkles and volume loss, particularly in the lower two thirds of the face (e.g., the nasolabial fold area). Dermal and subdermal filler injections can produce immediate results, but usually with limited duration of action.

Fillers can be classified based on their source (e.g., autologous, biological, or synthetic), based on duration of action (in number of months), and based on degree of reversibility (e.g., rapidly reversible, slowly biodegradable but not reversible, and nonbiodegradeable).

Desirably, dermal fillers are biocompatible, nonantigenic, nontoxic, noncarcinogenic and nonteratogenic. In addition, dermal fillers desirably produce consistent and reproducible outcomes with minimal migration from the injection site, maximal safety, minimal adverse effects (e.g., pain or stinging during injection, acute inflammation, infection, bruising, swelling, tenderness, skin discoloration delayed (>24 hrs) hypersensitivity or inflammation), retention of softness or flexibility in the tissue after injection, and ease of administration. Furthermore it is desirable to use a filler composition that is not permanent, yet provides adequate duration of effect, on the order of 12 months or more, so as to minimize the need for retreatment and the associated costs, along with good filler persistence (e.g., without development of nodules, hard lumps, or tenderness). While dermal fillers are known that provide some of these desirable properties, no single filler possesses all of these characteristics.

U.S. Pat. No. 7,968,110, entitled "Tissue augmentation material and method," teaches a tissue augmentation material comprising smooth rounded, substantially spherical particle of hydroxyapatite having a particle size large enough to avoid phagocytosis (i.e., larger than 15 microns) with a preferred particle size range of 30 to 150 microns to facilitate injection. The inventors teach spray drying a slurry of 20 to 40% hydroxyapatite to produce the hydroxyapatite particles having a particle size distribution between 38 to 63 microns that are of very high density (e.g., about 95% to 100%).

The present invention relates to a biocompatible filler composition (e.g., a dermal or subdermal filler composition) comprising porous calcium phosphate particles having a small particle size in combination with a thermoreversible gelling agent that is nontoxic, provides improved flexibility, and a long duration of effect.

BRIEF SUMMARY OF THE INVENTION

The invention provides an injectable tissue filler composition comprising, or consisting essentially of, (a) about 10% to about 75% calcium phosphate particles, based on the weight of the filler composition, wherein the calcium phosphate particles have a porosity of about 10% to about 90%, a surface area of about 1 $m^2/g$ to about 100 $m^2/g$, and a particle size of about 1 micron to about 30 microns, (b) about 0.5% to about 50% thermoreversible gelling agent, wherein the gelling agent is a hydrogel that is in the form of a liquid at 25° C. and in the form of a gel having a viscosity of about 2000 cP or more at 35° C., and (c) water and a buffering agent, wherein the filler composition has a pH of about 6.5 to about 7.5. Optionally the filler composition of the invention further comprises about 0.1% to about 30% of a persistence enhancer and/or volumizing agent.

The invention further provides a method of tissue augmentation comprising (i) obtaining an injectable filler composition of the invention and (ii) injecting or implanting the filler composition into or underneath dermal tissue to form a bleb (or blister), wherein the formation of the bleb or blister restores or increases tissue volume (e.g., soft tissue volume) in the region of injection or implantation. In a preferred embodiment the method results in tissue augmentation that persists for about 6 months or more (e.g., about 9 months or more, or about 12 months or more) without significant loss of volume, shape and texture (e.g., pliability or moldability).

The invention also provides a method of producing calcium phosphate particles having a rounded morphology comprising (i) providing calcium phosphate particles having a particle size of 30 micron or less and a surface area of 20 $m^2/g$ or less, and (ii) contacting the calcium phosphate particles with an acid selected from the group consisting of nitric acid, hydrochloric acid, sulfuric acid, and phosphoric acid, in water. The invention further provides a method of producing an injectable tissue filler composition comprising: (i) partially sintering calcium phosphate particles having a particle size of 30 micron or less and a surface area of 20 $m^2/g$ or less, (ii) contacting the partially sintered calcium phosphate particles with an acid selected from the group consisting of nitric acid, hydrochloric acid, sulfuric acid, and phosphoric acid, in water to form calcium phosphate particles have a rounded morphology, a porosity of about 10% to about 90%, a surface area of about 1 $m^2/g$ to about 100 $m^2/g$, and a mean particle size of about 1 micron to about 30 microns, and (iii) compounding the calcium phosphate particles with a thermoreversible gelling agent that is a hydrogel that is in the form of a liquid a 25° C. and in the form of a gel having a viscosity of about 2000 cP or more at 35° C., and an aqueous carrier.

DETAILED DESCRIPTION OF THE INVENTION

The present invention is directed to an injectable filler composition comprising, or consisting essentially of, calcium phosphate particles, a gelling agent, a carrier comprising water and an optional persistence enhancer and/or volumizing agent. The filler composition is biocompatible and can be injected through an 18 gauge or smaller opening needle. The filler composition is suitable for use in dermal and subdermal filler applications. For example, the filler composition can be used to restore tissue volume and/or to smooth out tissue defects (e.g., soft-tissue augmentation).

The filler composition is a thin cream before administration, but gels under physiological conditions. Thus, the filler composition of the invention can be introduced into the body in a minimally invasive manner prior to solidifying or gelling within the desired tissue, organ, or body cavity. Gelation occurs in situ after a change in temperature (i.e., a temperature induced phase transition).

The filler composition of the present invention comprises calcium phosphate particles that are biodegradable but are resistant to resorption by the body (i.e., are slowly resorbed or are substantially nonresorbable). Upon injection at the tissue site, the calcium phosphate particles provide a matrix or scaffolding, which is maintained by the presence of the gelling agent and optional persistence enhancer and/or volumizing agent.

Desirably the calcium phosphate particles are selected from the group consisting of hydroxyapatite, tricalcium phosphate (e.g., α-TCP, β-TCP or mixtures thereof), monocalcium phosphate monohydrate (MCPM), monocalcium phosphate (MCP), brushite, monetite, calcium carbonate, calcium carbonate apatite, octacalcium phosphate (OCP), tetracalcium phosphate (TTCP), calcium pyrophosphate, calcium fluorapatite, aluminas, and mixtures thereof. Preferably the calcium phosphate particles comprise, consist essentially of, or consist of hydroxyapatite, β-TCP, OCP, calcium carbonate, MCPM, MCP, brushite, monetite, or mixtures thereof. More preferably the calcium phosphate particles comprise, consist essentially of, or consist of hydroxyapatite, β-TCP, OCP, or mixtures thereof. Preferred combinations include mixtures of hydroxyapatite with a second calcium phosphate particle (e.g. β-TCP or MCPM), or mixtures of β-TCP and MCPM.

In some preferred embodiments, the calcium phosphate particles are partially or fully sintered particles (e.g., partially sintered hydroxyapatite particles) so as to impart improved mechanical robustness. Typically the calcium phosphate particles are heat treated at a temperature of about 800° C. to about 1200° C. (e.g., about 900° C. to about 1100° C., or about 950° C. to about 1050° C., or about 1000° C.) to crystallize and partially sinter the crystals to obtain mechanical robustness.

The calcium phosphate particles are characterized by being porous, preferably having a porosity of at least about 10%, more preferably at least about 20%, and even more preferably at least about 30%, by volume. Typically the calcium phosphate particles have a porosity less than about 90%, or less than 80%, by volume. In particularly preferred embodiments, the calcium phosphate particles have a porosity of about 5% to about 95%, or about 10% to about 90%, or about 20% to about 85%, or about 30% to about 75%, or about 40% to about 60%. Porosity can be determined by any suitable technique.

The calcium phosphate particles desirably are characterized by a generally rounded morphology such as spheroidal particles (i.e., having an aspect ratio of 1:1 to 5:1, preferably 1:1 to 3:1, or more preferably 1:1 to 2.5:1). Such rounded particles lead to reduced abrasion and irritation upon injection.

The calcium phosphate particles are further characterized by a mean particle size of about 1 microns to about 30 microns, preferably about 1.5 micron to about 20 microns, more preferably about 2 microns to about 10 microns. Desirably the particle size distribution of the calcium phosphate particles is about 0.1 micron to about 50 microns, or about 0.5 micron to about 35 microns, or about 1 micron to about 25 microns. Preferably about 80% or more, more preferably about 85% or more, or about 90% or more, or about 95% or more, of the particles are within the desired particle size range. Preferably, the mean particle size and particle size distribution is determined by laser scatter or diffraction, or by electron microcopy (e.g., TEM or SEM).

The calcium phosphate particles preferably are further characterized by an average crystal size of about 300 nm or less, preferably about 250 nm or less, more preferably about 200 nm or less, and about 5 nm or more, or about 10 nm or more, or about 20 nm or more, or about 30 nm or more. Typically the calcium phosphate particles have a mean crystal size of about 30 nm to about 200 nm, as determined by electron microcopy (e.g., TEM or SEM) or other suitable technique. Small crystal sizes are desirable to bind various proteins secreted by the surrounding tissue, thus strengthening the scaffold by encouraging connective tissue ingrowth.

To achieve the desired particle size and morphology, the calcium phosphate particles can undergo surface refining or smoothing by a milling operation, such as ball milling. Alternatively, the calcium phosphate particles can be produced by a spray drying technique, wherein the particles are obtained by spraying drying submicron calcium phosphate particles prepared by means known in the art such as low temperature crystallization methods, hydrothermal crystallization methods, solid-solid reactions and the like. Such particles can be spray dried optionally in the presence of a suitable wetting agent or binder. One method of spray drying is taught in U.S. Pat. No. 7,968,110. However, when the calcium phosphate particles used in the spray drying process are of high surface area, such as hydroxyapatite prepared according to the process described in U.S. Pat. No. 6,013,591, this process produces spherical smooth calcium phosphate particles in low yields having small particle sizes (e.g., 12 to 15 microns) and high densities, which can collapse after injection after the carrier solution dissipates allowing the spherical particles to adopt a close packing configuration. Such spray dried calcium phosphate particles act as poor volumizers and dermal fillers per unit mass.

In preferred embodiments, the calcium phosphate particles are surface treated by an acid etching technique in which the particles are exposed to aqueous acid mixture (e.g., nitric acid, sulfuric acid, hydrochloric acid, phosphoric acid, perchloric acid, and the like) for a period of time (e.g., 1 minutes or more, or 10 minutes or more, or 20 minutes or more, or 30 minutes or more, or 60 minutes or more) so as to remove any sharp or edged morphology on the particles and to remove particles of small particle size (e.g., less than 1 micron). In especially preferred embodiments, the calcium phosphate particles are both heat treated (i.e., partially or fully sintered) as described above and acid etched.

Figure 1:
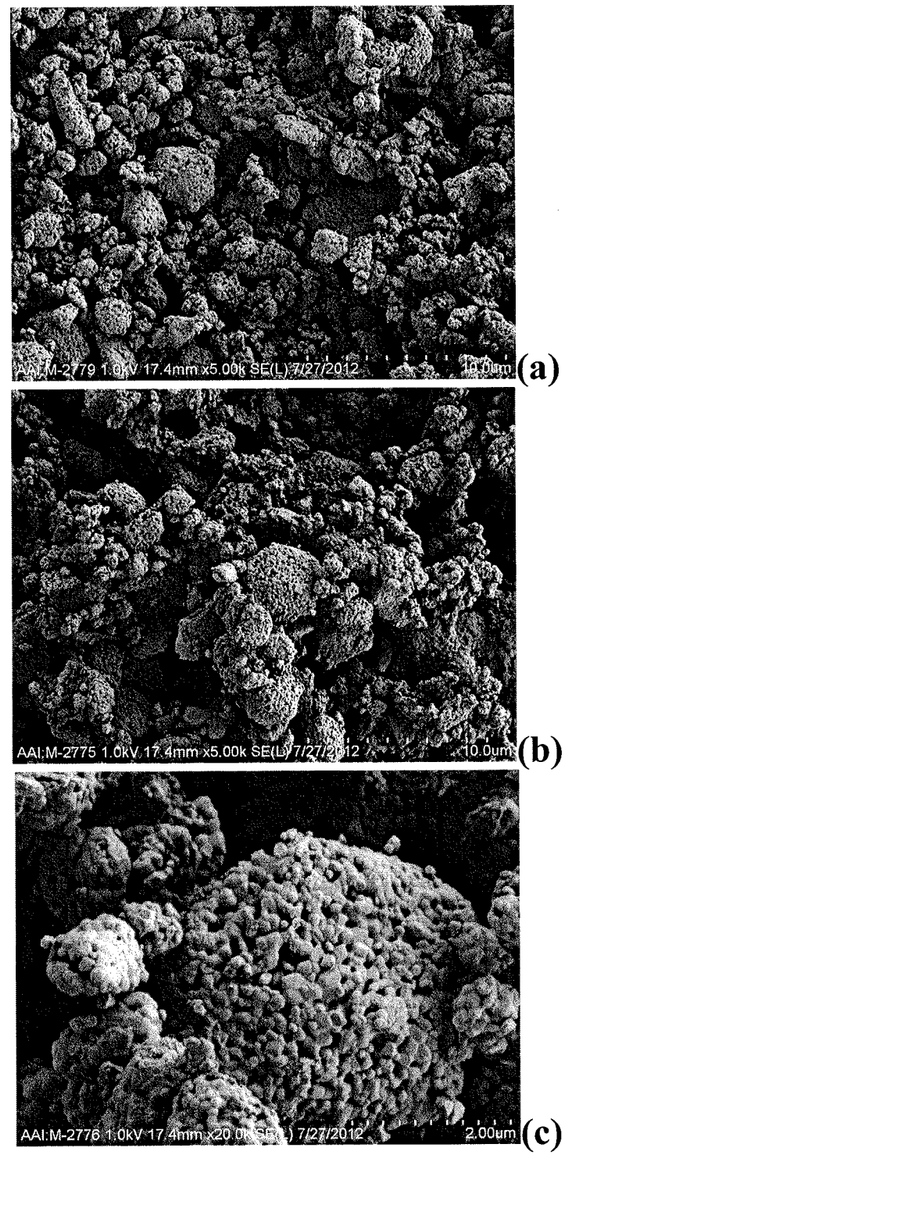
FIG. 1 is a series of SEM micrographs of acid etched, partially sintered porous, nanocrystalline hydroxyapatite particles (shown at different levels of magnification) that can be used in the filler composition of the invention.

Accordingly the invention also provides a method of producing calcium phosphate particles having a rounded morphology comprising (i) providing calcium phosphate particles having a particle size of 30 micron or less and a surface area of 20 m²/g or less, and (ii) contacting the calcium phosphate particles with an aqueous acid mixture (e.g., containing an acid selected from the group consisting of nitric acid, hydrochloric acid, sulfuric acid, phosphoric acid and perchloric acid, in water) for about 1 minutes or more, or 10 minutes or more, or 20 minutes or more, or 30 minutes or more, or 60 minutes or more. SEM micrographs of heat treated and acid etched porous hydroxyapatite powders prepared according to the method of the invention, that can be used in the filler composition of the invention, are shown in FIG. 1.

The calcium phosphate particles desirably are further characterized by a BET surface area of about 1 m²/g to about 100 m²/g, preferably about 1 m²/g to about 50 m²/g, preferably about 1 m²/g to about 20 m²/g. High surface area is desirable to bind various proteins secreted by the surrounding tissue, thus strengthening the scaffold by encouraging connective tissue ingrowth.

When the calcium phosphate particles are hydroxyapatite particles, preferably they are prepared by a wet chemical method involving (i) precipating apatite by adding a calcium source (e.g., calcium nitrate, preferably at a concentration of less than about 1 M) to a phosphate source (e.g., diammonium hydrogen phosphate), wherein the pH of the mixture is about 7 to about 14 (e.g., the pH is about 11 to about 13), (ii) aging the precipitated apatite (e.g., at a temperature of about 20° C. for at least about 12 hours), controlling the conditions of (i) and (ii) so as to produce an apatite precipitate having the desired average crystal size, (iv) collecting the apatite precipitate, and (v) drying the apatite precipitate to obtain the particulate apatite, and optionally (vi) wet grinding the precipitated apatite, as described in U.S. Pat. No. 6,013,591, which is incorporated by reference herein.

When the calcium phosphate particles are tricalcium phosphate, preferably they are prepared by a wet chemical method involving (i) precipating a TCP precursor material (e.g., monetite ($CaHPO_4$), brushite ($CaHPO_4.2H_2O$), hydroxyapatite, amorphous calcium phosphate, octacalcium phosphate, or combinations thereof), (ii) recovering the TCP precursor material, (iii) milling the TCP precursor material to form a powder in which the TCP precursor crystals are agglomerated to a minimal extent, and (iv) transforming the TCP precursor powder to form TCP, as described in U.S. Pat. No. 8,029,755, which is incorporated by reference herein. Precursor type, precursor concentration, solvent environment, addition rate of precursors, aging time, aging temperature, and pH during precipitation have been identified as the processing parameters controlling the molecular and structural development of TCP precursor materials.

The properties of the calcium phosphate particles (e.g., crystal size, particle size, surface area and porosity) desirably are selected so as to provide the highest occluded volume per unit mass while resisting collapse of the particle matrix or scaffolding.

The amount of the calcium phosphate particles present in the filler composition of the invention is selected so as to achieve the desired viscosity of the composition. Typically the filler composition contains about 10% to about 75% by weight calcium phosphate particles, based on the total weight of the filler composition. Preferably the filler composition contains about 20% to about 70%, or about 30% to about 60%, or about 40% to about 50% by weight calcium phosphate particles, based on the total weight of the filler composition.

The filler composition of the invention further comprises a hydrophilic gelling agent (e.g., a hydrogel) that is thermoreversible. Desirably the gelling agent exists as a liquid at room temperature and as a gel above its sol-gel transition temperature at or near body temperature, e.g., at about 35° C. to about 37° C. Thus the gelling agent desirably has a gelling temperature interval between about 25° C. and about 37° C. The gelling agent desirably further has a critical gel concentration that is less than about 40%, preferably less than about 30%, or less than about 20%. Desirably the viscosity (dynamic) of the gelling agent increases once it transitions into a gel state at body temperature and at the concentration used in the dermal filler, achieving a high gel viscosity. For example, the gelling agent desirably achieves a gel viscosity of about 2000 cP or more, or about 4000 cP or more, or about 5000 cP or more, or about 6000 cP or more, as measured with a HBDV-III Cone/Plate using spindle CP40 or CP51 at about 77° C.

Desirably the thermoreversible gelling agent has a high molecular weight that is resistant to metabolism in the body. For example, desirably the gelling agent has an average molecular weight of about 8,000 g/mol or more, preferably about 10,000 g/mol or more, or more preferably about 12,000 g/mol or more. In some embodiments it is preferred that the gelling agent also has a molecular weight of about 30,000 g/mol or less, preferably about 25,000 g/mol or less, or more preferably 20,000 g/mol or less.

The thermoreversible gelling agent can be any suitable compound. Known thermoreversible gelling agents in the art include poly(ethylene-b-propylene oxide-b-ethylene oxide) (poloxamer) and its copolymers, polysaccharides, N-isopropylacrylamide copolymers, hydrogels based on lactic acid, and thermosensitive liposome-based systems. In a preferred embodiment, the gelling agent is a poloxamer.

Suitable poloxamer include those containing a block copolymer having a middle block of poly(propylene oxide) with a molecular weight of from about 1450 to about 6000 g/mol, and end blocks of poly(ethylene oxide) that comprise about 50% to about 90% by weight of the copolymer. For example, the poloxamer can be selected from the group consisting of poloxamer 407, poloxamer 338, poloxamer 188, mixtures thereof, and graft copolymers thereof with poly(acrylic acid) or poly(methacrylic acid). Preferably the poloxamer is poloxamer 407.

Suitable polysaccharides include certain methyl cellulose, hydroxypropylmethylcellulose, and ethyl(hydroxyethyl)cellulose polymers that when modified by inclusion of suitable surfactants (e.g., sodium dodecyl sulfate or cetyl triammonium bromide) exhibit a phase transition at or slightly below body temperature accompanied by an increase in viscosity. In addition xyloglucan that has been partially degraded by beta-galactosidase and certain chitosan/polyol salt (e.g., β-glycerophosphate) combinations can be used.

Suitable N-isopropylacrylamide copolymers include poly (N-isopropylacrylamide-co-acrylic acid), poly(N-isopropylacrylamide-co-poly(ethylene oxide).

Suitable hydrogels based on poly(lactic acid) include poly(ethylene oxide)/(D,L-lactic acid-co-glycolic acid) copolymers such as PEO-b-(D,L-lactic acid-c-glycolic acid)-b-PEO triblock copolymers.

Suitable liposome-based systems include those based on alginates which form gels in the presence of multivalent ions such as calcium ($Ca^{2+}$).

The amount of the gelling agent present in the filler composition of the invention is selected so as to achieve the desired viscosity of the composition. Typically the filler composition contains about 0.5% to about 50% by weight gelling agent, based on the total weight of the filler composition. Preferably the filler composition contains about 1% to about 40%, or about 5% to about 30%, or about 8% to about 20% gelling agent, based on the total weight of the filler composition.

The filler composition of the invention optionally further comprises an agent (i.e., a persistence enhancer and/or volumizing agent) which acts to modify the gel properties of the gelling agent (e.g., to modify the sol gel transition temperature or viscosity) and/or stabilize the filler composition against loss of volume over time. Preferably the persistence enhancer and/or volumizing agent is hydrophilic, has a high average molecular weight and viscosity, and is not thermoreversible. The persistence enhancer and/or volumizing agent desirably is further an osmotic agent that draws in water to the filler composition.

The persistence enhancer and/or volumizing agent ("persistence enhancer") can be any suitable additive(s), including methyl cellulose, carboxymethylcellulose, dextran, carrageenan, agarose, gelatin, collagen, block copolymers based on ethylene oxide and propylene oxide (e.g., Pluronic 25R4), polyethylene glycol (e.g., PEG having an average molecular weight of 5000 or more, or 10,000 or more, or 50,000 or more), polyoxyethylene derivatives of sorbitan monolaurate (e.g., polysorbate 20 and polysorbate 80), ethylene oxide/propylene oxide block copolymers (e.g., those sold as Tetronic® copolymers), polyether polyols (e.g., those sold as Tergitol® copolymers), polyacrylic acid polymers (e.g., Carbopol polymers such as Carbopol 934P, a high molecular weight polymer of acrylic acid cross-linked with allyl ethers of sucrose or pentaerythritol), or mixtures thereof.

Preferably the persistence enhancer is a dextran having a number average molecular weight of 50,000 g/mol or more (e.g., about 100,000 g/mol or more, or even about 500,000 g/mol or more). For example suitable dextrans include dextran 70, dextran 110, dextran 500, dextran 2000 and combinations thereof, wherein dextran 500 is preferred.

The amount of the persistence enhancer present in the filler composition of the invention is selected so as to achieve the desired viscosity of the composition at the desired sol gel temperature. Typically the filler composition contains about 0.1% to about 30% by weight persistence enhancer, based on the total weight of the filler composition. Preferably the filler composition contains about 0.5% to about 25%, or about 1% to about 20%, or about 2% to about 15% by weight persistence enhancer, based on the total weight of the filler composition.

Optionally the filler composition of the invention further comprises a lubricant. Suitable lubricants include glycerol, glycerol monoacetate, glycerol diacetate, glycerol triacetate, polyethylene glycol 300, polyethylene glycol 400, gelatin, uncross-linked hyaluronic acid, and combinations thereof. Typically the filler composition of the invention contains lubricant in the amount of about 0.5% to about 10%, preferably about 1% to about 8%, or about 2% to about 6%, or about 3% to about 5%, based on the total weight of the filler composition.

The filler composition comprises an aqueous carrier. It is understood that the carrier can include additional components suitable to the particular formulation. For example, in certain embodiments, the filler composition of the invention can be formulated to include pharmaceutically acceptable excipients such as buffers, e.g., phosphate buffered saline (PBS) solutions and/or $Na_2HPO_4$, physiological saline buffers such as Hanks's solution and Ringer's solution, various solvents, and salts, etc. Desirably the filler composition of the invention has a neutral pH, e.g., a pH of about 6.5 to about 7.5.

The amount of carrier present in the filler composition of the invention can vary, and is selected so as to achieve the desired viscosity of the composition. Typically the filler composition contains about 1% to about 70% by weight carrier, based on the total weight of the filler composition. Preferably the filler composition contains about 5% to about 60%, or about 15% to about 50%, or about 20% to about 40% by weight carrier, based on the total weight of the filler composition.

Optionally the filler composition of the invention further includes additional agents such as one or more therapeutic and/or cosmetic agents selected from the group consisting of analgesics, antimicrobial agents, antiseptics (e.g., selected from the group consisting of chlorhexidine gluconate, benzalkonium chloride, cetyl trimethylammonium bromide, cetylpyridinium chloride, benzethonium chloride, alcohol, sodium chloride and sodium bicarbonate), hormones, enzymes, antiallergic agents, antibiotics, steroidal anti-inflammatory agents, non-steroidal anti-inflammatory agents (e.g., ibuprofen or a pharmaceutically acceptable salt thereof), cytokines, growth factors, antineoplastic agents, anaesthetics (e.g., selected from the group consisting of lidocaine, lignocaine and prilocaine), astringents, immunosuppressants, anticoagulants, anticoagulation factors, clotting factors, anti-oxidants, anti-aging agents (e.g., selected from the group consisting of retinol, retinal, retinyl palmitate, retinyl acetate, other esters of retinol, retinoic acid, other retinoids, collagen, vitamin E, vitamin C, other vitamins, idebenone, peptides, pentapeptides, polypeptides, transcription factors, UV blockers and mixtures thereof) and mixtures thereof.

In certain preferred embodiments, the filler composition comprises, or consists essentially of, about 30% to about 50% (e.g., about 35-45%) hydroxyapatite particles (e.g., partially sintered and acid etched), about 5% to about 15% (e.g., about 8-12%) poloxamer 407, about 2% to about 8% (e.g., about 4-6%) dextran 500, and about 40% to about 50% (e.g., about 42-48%) carrier containing phosphate buffered saline, $Na_2HPO_4$, glycerol (e.g., about 2% to 6%), and water, based on the total weight of the filler composition.

The filler composition of the invention can be prepared by standard techniques known in the art. Typically a concentrate of the carrier is prepared and then blended with the thermoreversible gelling agent and other additives (e.g., a persistence enhancer). The calcium phosphate particles are then compounded with the carrier/gelling agent preparation. In preferred embodiments, the filler composition is prepared by a method comprising: (i) partially sintering calcium phosphate particles having a particle size of 30 micron or less and a surface area of 20 $m^2$/g or less, (ii) contacting the partially sintered calcium phosphate particles with an acid selected from the group consisting of nitric acid, hydrochloric acid, sulfuric acid, and phosphoric acid, in water for about 30 minutes or more to form calcium phosphate particles have a rounded morphology, a porosity of about 10% to about 90%, a surface area of about 1 $m^2$/g to about 100 $m^2$/g, and a mean particle size of about 1 micron to about 30 microns, and (iii) compounding the calcium phosphate particles with a thermoreversible gelling agent that is a hydrogel that is in the form of a liquid a 25° C. and in the form of a gel having a viscosity of about 2000 cP or more at 35° C., optional persistence enhancer, and aqueous carrier.

The filler composition of the invention desirably is used in a method of tissue (e.g., soft tissue) augmentation comprising injecting or implanting (e.g., using a syringe and needle, etc.) the biocompatible filler composition into or underneath the tissue at an augmentation site (e.g., subcutaneous administration, intradermal administration, subdermal administration or administration onto or into bone) to form a bleb (or blister). The filler composition of the invention can also be injected or implanted superficially, such as, for example, within the papillary layer of the dermis, or can be injected or implanted within the reticular layer of the dermis. Accordingly the invention is further directed to a method of tissue augmentation comprising (i) obtaining an injectable filler composition of the invention and (ii) injecting or implanting the filler composition into or underneath dermal tissue to form a bleb, wherein the formation of the bleb restores or increases tissue volume in the region of injection or implantation.

The filler composition of the invention provides improved ease of injection through a minimum of a 18 gauge needle (or 22 gauge, or 27 gauge needle), reduced pain or stinging during injection, no immediate acute inflammation, no delayed (>24 hours) hypersensitivity or inflammation, retention of pliability, moldability and/or flexibility after injection into the face or body, no migration of filler after injection, persistence for several months or longer and no nodularity or hard lumps or tenderness. Desirably the filler composition demonstrates a volume retention of about 6 months or more, preferably about 9 months or more, and even more preferably about 12 months or more, with good pliability, moldability and/or flexibility and biocompatibility. Thus, in a preferred embodiment, the method of tissue augmentation results in tissue augmentation that persists for about 6 months or more (e.g., about 9 months or more, or about 12 months or more) without significant loss of volume, shape and texture (e.g., pliability or moldability).

The persistence of the filler composition can be measured, e.g., by visual or palpable assessment, for example, using Global Aesthetic Improvement Scale (GAIS) ratings. GAIS is based on a physician's assessment of the overall improvement, e.g., cosmetic improvement, in a treated area, e.g., nasolabial fold, by comparing the patient's appearance after treatment to that before treatment. GAIS ratings include: very much improved (optimal cosmetic result for the implant in the patient); much improved (marked improvement in appearance from the initial condition, but not completely optimal for this patient); improved (obvious improvement in appearance from initial condition); no change (the appearance is essentially the same as the original condition); and worse (the appearance is worse than the original condition).

One of skill in the art will appreciate that the viscosity and/or elasticity of the filler composition in vivo can be adjusted to achieve greater volumizing action and longer persistence, e.g., through increase solids loading or through selection of a thermoreversible gelling agent and optional persistence enhancer and/or volumizing agent that will provide increased viscosity upon injection. Desirably the filler composition of the invention has a high viscosity on the order of about 100,000 cP to about 200,000 cP, or about 120,000 cP to about 180,000 cP, or about 140,000 cP to about 160,000 cP. The viscosity of the filler composition can be determined by measuring the force needed to push the material through a ¾"×28 gauge needle, converting the force to a pressure based on the diameter of the cylinder and piston used to create the flow, and back calculating using the Hagen-Poiseuille equation. Desirably the filler composition of the invention has a high elastic modulus (G') on the order of about 200 Pa to about 500 Pa, or about 220 Pa to about 450 Pa, or about 250 Pa to about 400 Pa (measured at 10 rads/sec).

Cosmetic uses of the filler composition of the invention include treatment of fine lines, such as fine superficial facial lines, wrinkles, grooves, creases, and scars, as well as treatment of pronounced lines, wrinkles, and scars. In some aspects, the filler composition of the invention is used for other cosmetic uses, including treatment for or reducing transverse forehead lines, glabellar frown lines, nasolabial fold, vermilion border, periorbital lines, vertical lip lines, oral commissure, etc., as well as defining the lip border. The filler composition of the invention is also useful for correcting contour deformities and distensible acne scars, or for treating other tissue defects, such as, for example, atrophy from disease or trauma or surgically-induced irregularities, correction and restoration of facial fat loss (lipoatrophy), for example in patients with HIV. The method of treatment comprises providing a filler composition of the invention and injecting or implanting the composition into the skin or deep tissue.

In other embodiments, the filler composition of the present invention is used for surgical procedures involving tissue augmentation, tissue repair, or drug delivery. In some aspects, the filler composition is used for tissue augmentation in conditions such as urinary incontinence, vasicoureteral reflux, and gastroesophageal reflux. For example, the filler composition of the invention can be used to add tissue bulk to sphincters, such as a gastric or urinary sphincter, to provide proper closure and control. In instances of urinary incontinence, such as stress incontinence in women or incontinence following a prostatectomy in men, the filler composition of the invention can be provided to further compress the urethra to assist the sphincter muscle in closing, thus avoiding leakage of urine from the bladder.

Similarly, gastroesophageal reflux disease (GERD, also known as peptic esophagitis and reflux esophagitis) is a disorder that affects the lower esophageal sphincter, the muscle connecting the esophagus with the stomach. GERD occurs when the lower esophageal sphincter is incompetent, weak, or relaxes inappropriately, allowing stomach contents to flow up into the esophagus (i.e., reflux). Malfunction of the lower esophageal sphincter muscles, such as that resulting from muscle tonal loss, can lead to incomplete closure of the lower esophageal sphincter, causing back up of acid and other contents from the stomach into the esophagus. Poor response to dietary modification or medical treatment may require surgery to correct the dysfunction. In one embodiment, the filler composition of the present invention is used in such procedures and, for example, is injected into the area of the esophageal sphincter to provide bulk to the lower esophageal sphincter.

In other embodiments, the filler composition of the invention is used to fill or block voids and lumens within the body. Such voids may include, but are not limited to, various lesions, fissures, diverticulae, cysts, fistulae, aneurysms, or other undesirable voids that may exist within the body; and lumens may include, but are not limited to, arteries, veins, intestines, Fallopian tubes, and trachea. For example, the filler composition of the invention can be administered into the lumen or void to provide partial or complete closure, or to facilitate repair of damaged tissue.

In other aspects, tissue repair is achieved by providing the filler composition of the invention to an area of tissue that has been diseased, wounded, or removed. In some embodiments, the filler composition of the invention is used to fill in and/or smooth out soft tissue defects such as pockmarks or scars. In such cases, the filler composition of the invention is injected beneath the imperfection. The improved persistence of the filler composition of the invention would be beneficial, e.g., by reducing the number and frequency of treatments required to obtain a satisfactorily result. In certain embodiments, the filler composition is used for intracordal injections of the larynx, thus changing the shape of this soft tissue mass and facilitating vocal function. Such use is specifically contemplated for the treatment of unilateral vocal cord paralysis. Further, the present invention contemplates use of the filler composition in mammary implants, or to correct congenital anomalies, acquired defects, or cosmetic defects.

The filler composition of the invention can also be used in various surgical or other procedures for remodeling or restructuring of various external or internal features, e.g., plastic surgery for corrective or cosmetic means, etc.

In any of the embodiments described above, the filler composition of the invention may be used for drug delivery, for example, to deliver drugs to an injection site. Drugs delivered in this manner may thus enhance tissue repair, and could provide additional therapeutic benefit.

In additional embodiments, the invention further contemplates incorporation of cells into the filler composition of the invention to provide a means for delivering cells to repopulate a damaged or diseased tissue or to provide products synthesized by the cells to the tissues surrounding the injection site.

The following examples further illustrate the invention but, of course, should not be construed as in any way limiting its scope.

Examples 1-5

A first filler composition comprising hydroxyapatite, prepared according to the method described in U.S. Pat. No. 6,013,591 and calcined at 300° C., 10% Poloxamer 407 and DI water was prepared. When injected subdermally, inflammation and redness at the injection site was noted several hours after injection.

A second filler composition comprising hydroxyapatite, prepared according to the method described in U.S. Pat. No. 6,013,591 and calcined at 300° C., 10% Poloxamer 407 and phosphate buffer solution was prepared. When injected subdermally, inflammation and redness at the injection site was noted several hours after injection. This inflammation and redness is though to be connected to the chemistry and surface morphology of the HA.

A third filler composition comprising hydroxyapatite, prepared according to the method described in U.S. Pat. No. 6,013,591 and calcined at 300° C., phosphate buffer solution and $Na_2HPO_4$ buffer was prepared. The very high surface area of the nanocrystalline HA results in a high dissolution rate and leaching of calcium ions, resulting an acidic pH. The $Na_2HPO_4$ buffer was added to counteract the acidic pH. However the pH of the dermal filler was still acidic. When injected subdermally, immediate inflammation and redness at the injection site occurred. Injection was painful as well.

A fourth filler composition comprising hydroxyapatite, prepared according to the method described in U.S. Pat. No. 6,013,591 and calcined at 1000° C., phosphate buffer solution and $Na_2HPO_4$ buffer was prepared. A higher calcination temperature was used to decrease the surface area to reduce the acidic pH. The $Na_2HPO_4$ buffer was added to counteract the acidic pH. When injected subdermally, inflammation and redness at the injection site occurred several hours after injection.

A fifth filler composition comprising hydroxyapatite, prepared according to the method described in U.S. Pat. No. 6,013,591 and calcined at 1000° C., phosphate buffer solution, $Na_2HPO_4$ buffer and glycerol was prepared. Glycerol was used a solvent to reduce the solubility of the nanocrystalline HA and the acidic pH effect as well as to act as a lubricant during injection. When injected subdermally, inflammation and redness at the injection site occurred several hours after injection.

SUMMARY OF EXAMPLES 1 to 5: Though the pH was successfully buffered at a neutral pH, inflammation and redness still occur. Conclusions that can be drawn from the above experiments include: (1) Acidic or basic pHs can cause pain during injection as well inflammation and redness at the injection site. Neutral pHs are preferred. (2) The HA itself seems to cause redness and inflammation in it of itself independent of dissolution and pH changes. The morphology of HA appears to "tear" the tissue during the injection. Results indicate that the morphology needs to be "softened." (3) The unique properties of the Poloxamer 407 (i.e., gelation at body temperature) appears to mask the negative effects associated with dissolution, pH change and particle morphology.

Examples 6-16

A sixth filler composition comprising 61% (solids, w/w) hydroxyapatite, prepared according to the method described in U.S. Pat. No. 6,013,591 and calcined at 1000° C. and acid etched with nitric acid, 20% Poloxamer 407, $Na_2HPO_4$ buffer and 5% glycerol was prepared. To alter the morphology of the nanocrystalline HA to reduce inflammation, the HA particles were "acid etched." Poloxamer 407 was used because of its beneficial effects (i.e. painless injection, reduction of inflammation). Glycerol was used a lubricant to assist in injecting through a 27 gauge needle. The $Na_2HPO_4$ buffer was added to counteract the acidic pH. When injected subdermally, there was no pain during injection, no inflammation and no redness at the injection site. However the formulation was difficult to inject through a 27 gauge needle and had too much back pressure.

A seventh filler composition comprising 67% (solids, w/w) hydroxyapatite, prepared according to the method described in U.S. Pat. No. 6,013,591 and calcined at 1000° C. and acid etched with nitric acid, 20% Poloxamer 407, $Na_2HPO_4$ buffer and 5% glycerol and 500,000 MW dextran was prepared to demonstrate maximum solid loading. The dextran was added to increase viscosity of carrier to enhance shelf stability and persistence after injection. When injected subdermally, there was no pain during injection, no inflammation and no redness at the injection site. However, the formulation was difficult to inject through a 27 gauge needle and had too much back pressure.

A eighth filler composition comprising 30% (solids, w/w) hydroxyapatite, prepared according to the method described in U.S. Pat. No. 6,013,591 and calcined at 1000° C. and acid etched with nitric acid, 20% Poloxamer 407, $Na_2HPO_4$ buffer, 5% glycerol and 500,000 MW dextran was prepared to determine if reducing solids loading would reduce the injection pressure. When injected subdermally, there was no pain during injection, no inflammation and no redness at the injection site. However the formulation was difficult to inject through a 27 gauge needle and had too much back pressure.

A ninth filler composition comprising 30% (solids, w/w) hydroxyapatite, prepared according to the method described in U.S. Pat. No. 6,013,591 and calcined at 1000° C. and acid etched with nitric acid, 20% Poloxamer 407, $Na_2HPO_4$ buffer, and 5% glycerol was prepared to determine if reducing solids loading and eliminating dextran would reduce the injection pressure. When injected subdermally, there was no pain during injection, no inflammation and no redness at the injection site. However, the formulation was difficult to inject through a 27 gauge needle and had too much back pressure. From this it was concluded that the high concentration of Poloxamer 407 resulted in the high injection pressure.

A tenth filler composition comprising 50% (solids, w/w) hydroxyapatite, prepared according to the method described in U.S. Pat. No. 6,013,591 and calcined at 1000° C. and acid etched with nitric acid, 17.5% Poloxamer 407, $Na_2HPO_4$ buffer, and 5% glycerol was prepared to determine if reducing Poloxamer 407 concentration would reduce the injection pressure. When injected subdermally, there was no pain during injection, no inflammation and no redness at the injection site. However, the formulation was difficult to inject through a 27 gauge needle and had too much back pressure.

A eleventh filler composition comprising 50% (solids, w/w) hydroxyapatite, prepared according to the method described in U.S. Pat. No. 6,013,591 and calcined at 1000° C. and acid etched with nitric acid, 15% Poloxamer 407, $Na_2HPO_4$ buffer, and 5% glycerol was prepared to determine if further reducing Poloxamer 407 concentration would reduce the injection pressure. When injected subdermally, there was no pain during injection, no inflammation and no redness at the injection site. However the formulation was difficult to inject through a 27 gauge needle and had too much back pressure.

A twelfth filler composition comprising 50% (solids, w/w) hydroxyapatite, prepared according to the method described in U.S. Pat. No. 6,013,591 and calcined at 1000° C. and acid etched with nitric acid, 15% Poloxamer 407, $Na_2HPO_4$ buffer, 5% glycerol and 5% dextran 500,000 MW was prepared to determine if the addition of dextran would reduce the injection pressure. When injected subdermally, there was no pain during injection, no inflammation and no redness at the injection site. However the formulation was difficult to inject through a 27 gauge needle and had too much back pressure.

A thirteenth filler composition comprising 50% (solids, w/w) hydroxyapatite, prepared according to the method described in U.S. Pat. No. 6,013,591 and calcined at 1000° C. and acid etched with nitric acid, 15% Poloxamer 407, $Na_2HPO_4$ buffer, 5% glycerol and 3% dextran 500,000 MW was prepared to determine if the addition of less dextran would reduce the injection pressure. When injected subdermally, there was no pain during injection, no inflammation and no redness at the injection site. However the formulation was difficult to inject through a 27 gauge needle and had too much back pressure.

A fourteenth filler composition comprising 40% (solids, w/w) hydroxyapatite, prepared according to the method described in U.S. Pat. No. 6,013,591 and calcined at 1000° C. and acid etched with nitric acid, 12.5% Poloxamer 407, $Na_2HPO_4$ buffer and 5% glycerol was prepared to determine if the reduced solids loading and Poloxamer 407 content would reduce the injection pressure. When injected subdermally, there was no pain during injection, no inflammation and no redness at the injection site. However the formulation was difficult to inject through a 27 gauge needle and had too much back pressure.

A fifteenth filler composition comprising 40% (solids, w/w) hydroxyapatite, prepared according to the method described in U.S. Pat. No. 6,013,591 and calcined at 1000° C. and acid etched with nitric acid, 10% Poloxamer 407, $Na_2HPO_4$ buffer, 5% glycerol and 5% dextran (500,000 MW) was prepared to determine if the reduced Poloxamer 407° Content and addition of dextran would reduce the injection pressure. When injected subdermally, there was no pain during injection, no inflammation and no redness at the injection site. In addition, the formulation was easily injected through a 27 gauge needle.

A sixteenth filler composition comprising 40% (solids, w/w) hydroxyapatite, prepared according to the method described in U.S. Pat. No. 6,013,591 and calcined at 1000° C. and acid etched with nitric acid, 10% Poloxamer 407, $Na_2HPO_4$ buffer, 5% glycerol and 2% agarose was prepared. When injected subdermally, there was no pain during injection, no inflammation and no redness at the injection site. In addition, the formulation was easily injected through a 27 gauge needle.

Example 17

This example illustrates preferred dermal filler compositions of the invention comprising acid etched hydroxyapatite and poloxamer 407 in combination with a persistence enhancer and/or volumizing agent.

Formulation 1
 Carrier (1 Liter)
 1 jar (~9.8 g) Dulbeco's phosphate buffered saline
 5.92 g $Na_2HPO_4$ Anhydrous (or 7.42 g $Na_2HPO_4.2H_2O$)
 950 ml RO/DI water
 50 ml Glycerol
 Modifiers
 12.5% (by weight with Carrier) Poloxamer 407
 Filler
 40% (by weight of Carrier+Modifiers) Acid Etched HA Formulation 2
 Carrier (1 Liter)
 1 jar (~9.8 g) Dulbeco's phosphate buffered saline
 5.92 g $Na_2HPO_4$ Anhydrous (or 7.42 g $Na_2HPO_4.2H_2O$)
 950 ml RO/DI water
 50 ml Glycerol
 Modifiers
 10% (by weight with Carrier) Poloxamer 407
 5% 500 k MW Dextran
 Filler
 40% (by weight of Carrier+Modifiers) Acid Etched HA Formulation 3
 Carrier (1 Liter)
 1 jar (~9.8 g) Dulbeco's phosphate buffered saline
 5.92 g $Na_2HPO_4$ Anhydrous (or 7.42 g $Na_2HPO_4.2H_2O$)
 950 ml RO/DI water
 50 ml Glycerol
 Modifiers
 10% (by weight with Carrier) Poloxamer 407
 2% Agarose (Ghimas)
 Filler
 40% (by weight of Carrier+Modifiers) Acid Etched HA Example 18

This example illustrates a method for preparing a filler composition of the invention comprising acid etched hydroxyapatite, poloxamer 407 and dextran 500.

Preparation of Dermal Filler Powder:

Hydroxyapatite (HA) (e.g., having 10-100 nm average crystal size, about 1-10 micron particle size, 150-220 m²/g surface area, and characterized by XRD as at least 95% HA) is calcined at 1000° C. for 2 hours with ramp rates of 5° C./minute. Once cooled the HA powder is jet milled to a particle size whereby 95% of the particles are between 2 and 10 microns.

The powdery mass is transferred to a beaker with a stirring rod and RO/DI (treated by a combination of Reverse Osmosis and De-Ionization) water (5×the mass of the powder ±25 ml) is added. The solution is allowed to mix at 500±rpm for 1 hour after which time it is added to an equal volume solution of 4 mM nitric acid. The mixture with nitric acid is allowed to mix for 1 hour after the nitric acid addition is complete. The mixture is then centrifuged for 15 minutes at approximately 5000 rpm. The liquid is removed and then RO/DI water (4×±25 mL the mass of powder) is added and shaken to disperse the powder. This step is repeated two more times with RO/DI water and then two more times with ethanol in place of the RO/DI water. After the last ethanol is removed, ethanol (1×the mass of powder) is added and shaken to disperse the powder. The ethanol mixture is poured over a 106 micron sieve and the liquid passing through is collected onto a clean porcelain tray. The tray and collected liquid are placed into an oven at 65±10° C. until dry.

Preparation of Dermal Filler Concentrate:

To a 500 ml beaker is added 1 jar (~9.8 g) Dulbeco's phosphate buffered saline, 5.92 g $Na_2HPO_4$ (anhydrous) or 7.42 g $Na_2HPO_4$ (dihydrate), 62.62 g glycerol, and 100±20 ml RO/DI water. The mixture is stirred until dissolved, using heat (up to 50° C.) as needed. The solution is transferred to a 250 ml volumetric flask and q.s. to 250 ml with RO/DI water and sterile filtered into a storage container.

Preparation of Dermal Filler:

25-50 ml of dermal filler concentrate is sterile filtered and placed into a sanitized jacketed reactor. RO/DI water (3×the amount of concentrate added ±1 g) is added to the jacketed reactor and the mixture is chilled to 2° C. and mixed as fast as possible without causing the stir bar to be decoupled from the stir plate or the solution to overflow. Poloxamer 407 and dextran 500 (i.e., 500,000 molecular weight) are added to the jacketed reactor and the mixture is allowed to mix at a high rate of speed for at least 2 hours. The amount of poloxamer 407 and dextran added depends on the desired concentrations according to the following equations and table:

x (desired wt. % poloxamer 407) = [(1/100 − (x + y))/100] * [4 * x/100];
y (desired wt. % dextran) = [(1/100 − (x + y))/100] * [4 * y/100]

| x | y | mass poloxamer/1 g dermal filler concentrate | mass dextran/1 g dermal filler concentrate |
|---|---|---|---|
| 10 | 5 | 0.471 | 0.235 |
| 10 | 6 | 0.476 | 0.286 |
| 10 | 7 | 0.482 | 0.337 |
| 12.5 | 5 | 0.606 | 0.242 |
| 15 | 5 | 0.750 | 0.250 |
| 17.5 | 5 | 0.903 | 0.258 |

The mixing is then stopped and the mixture is allowed to rest for ~2 hours to allow entrained air to escape. The mixture is then mixed for 1 hour at a slower speed to allow mixing but without incorporation of bubbles into the liquid.

Depyrogenated dermal filler powder (HA) is mixed by hand with sterile filtered poloxamer and dextran solution to form a coarse mixture. The mixture is then emulsified by subjecting the material to successively greater shear by pumping it through successively narrower opening, tubes or channels to finely disperse the hydroxyapatite particles within the gel carrier.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. An injectable soft tissue filler composition comprising
   (a) about 40% calcium phosphate particles, based on the weight of the filler composition, wherein the calcium phosphate particles have a porosity of about 10% to about 90%, a surface area of about 1 m²/g to about 100 m²/g, and a mean particle size of about 2 microns to about 10 microns, and are acid etched,
   (b) about 5% to about 15% poloxamer, based on the weight of the filler composition, wherein the poloxamer is a hydrogel that is in the form of a liquid at 25° C. and in the form of a gel having a viscosity of about 2000 cP or more at 35° C.,

(c) a persistence enhancer selected from the group consisting of dextran and agarose, and
(d) aqueous carrier,
wherein the soft tissue filler composition has a pH of about 6.5 to about 7.5,
wherein the soft tissue filler composition can be injected through a 27 gauge or smaller opening needle, and
wherein the soft tissue filler composition is pliable, moldable, flexible, and has a viscosity of about 100,000 cP to about 200,000 cP after injection into the soft tissue.

2. The filler composition of claim 1, wherein the calcium phosphate particles are selected from the group consisting of hydroxyapatite, tricalcium phosphate, octacalcium phosphate, and combinations thereof.

3. The filler composition of claim 1, wherein the calcium phosphate particles comprise hydroxyapatite.

4. The filler composition of claim 1, wherein the calcium phosphate particles have an average crystal size of about 300 nm or less.

5. The filler composition of claim 1, wherein the poloxamer contains a block copolymer having a middle block of poly(propylene oxide) with a molecular weight of from about 1450 g/mol to about 6000 g/mol, and end blocks of poly(ethylene oxide) that comprise about 50% to about 90% by weight of the copolymer.

6. The filler composition of claim 5, wherein the poloxamer has a polyoxypropylene molecular mass of 4,000 g/mol and a 70% polyoxyethylene content.

7. The filler composition of claim 1, wherein the persistence enhancer is a dextran having an average molecular weight of about 500,000 g/mol or greater.

8. The filler composition of claim 1, wherein the composition comprises about 0.1% to about 25% persistence enhancer, by weight of the filler composition.

9. The filler composition of claim 1, wherein the calcium phosphate particles have a rounded morphology.

10. The filler composition of claim 1, wherein the calcium phosphate particles comprise about 95% or more hydroxyapatite, wherein poloxamer is poloxamer 407, and wherein the persistence enhancer is dextran having an average molecular weight of about 500,000 g/mol or greater, glycerol, and a phosphate buffer.

11. The filler composition of claim 10, wherein the amount of dextran is about 2% to about 8%, the amount of glycerol is about 2% to about 6%, and the amount of aqueous carrier is about 40% to about 50%, based on the weight of the filler composition.

12. The filler composition of claim 1, wherein the amount of poloxamer is about 5% to about 10%.

13. The filler composition of claim 11, wherein the amount of poloxamer is about 5% to about 10%.

14. The filler composition of claim 12, wherein the poloxamer is poloxamer 407.

* * * * *